(12) United States Patent
Baron et al.

(10) Patent No.: US 12,727,886 B2
(45) **Date of Patent: *Sep. 8, 2026**

(54) SYSTEMS, METHODS AND DEVICES FOR CONNECTING NON-ADHERENT STRUCTURES

(71) Applicant: Boston Scientific Scimed, Inc., Maple Grove, MN (US)

(72) Inventors: Todd Baron, Chapel Hill, NC (US); Peter L. Dayton, Brookline, MA (US); Bryan Bannon, Duxbury, MA (US); Barry Weitzner, Acton, MA (US); Thomas Desimio, Alpine, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 32 days.

This patent is subject to a terminal disclaimer.

(21) Appl. No.: 18/802,150

(22) Filed: Aug. 13, 2024

(65) Prior Publication Data

US 2024/0398411 A1 Dec. 5, 2024

Related U.S. Application Data

(63) Continuation of application No. 17/164,329, filed on Feb. 1, 2021, now Pat. No. 12,082,815, which is a (Continued)

(51) Int. Cl.

*A61B 17/11* (2006.01)
*A61F 2/95* (2013.01)

(52) U.S. Cl.

CPC ............ *A61B 17/1114* (2013.01); *A61F 2/95* (2013.01); *A61B 2017/1139* (2013.01)

(58) Field of Classification Search

CPC ............ A61B 17/1114; A61B 17/3478; A61B 2017/0034; A61B 2017/00358;

(Continued)

(56) References Cited

U.S. PATENT DOCUMENTS 7,316,655 B2 1/2008 Garibotto et al.
10,130,502 B2 11/2018 Chamorro et al.

(Continued)

FOREIGN PATENT DOCUMENTS

CN 101083942 A 12/2007
JP 2006198434 A 8/2006

(Continued)

OTHER PUBLICATIONS

Tyberg et al., "Endoscopic ultrasound-guided gastrojejunostomy with a lumen metal stent: A multicenter international Experience," Endoscopy International Open, Issue 4, pp. E276-E281. 2016.

(Continued)

*Primary Examiner* — Jocelin C Tanner
(74) *Attorney, Agent, or Firm* — Seager, Tufte & Wickhem, LLP

(57) ABSTRACT

A system for forming an anastomosis between first and second sections of a digestive tract includes Optical Scope Device ("OSD") having a lumen extending therethrough and positioned at a first target site within the first section, OSD including an imaging component at a distal end thereof for viewing the first target site; First Endoscope ("FE") including a working channel extending therethrough and positioned at a second target site within the second section; Capture Device ("CD") extending from a proximal end to a distal end including a loop, CD extends through the lumen; First Flexible Element ("FFE") extends through FE, FFE including a coupling element which passes through the loop to couple FFE to CD, connecting the first and second sections, the coupling element moving between insertion and locking configurations; and Stent having a lumen extending therethrough which provides fluid communication between the first and second sections.

20 Claims, 6 Drawing Sheets

Related U.S. Application Data continuation of application No. 16/244,859, filed on Jan. 10, 2019, now Pat. No. 10,952,733.

(60) Provisional application No. 62/616,217, filed on Jan. 11, 2018.

(58) Field of Classification Search

CPC .... A61B 2017/1139; A61B 2017/3413; A61B 2017/1132; A61B 2017/1135; A61B 2017/1117; A61B 2017/1121; A61B 2090/3784; A61F 2/90; A61F 2/95; A61F 2250/0039

USPC .......................................................... 606/153

See application file for complete search history.

(56) References Cited

U.S. PATENT DOCUMENTS

| | | | |
|---|---|---|---|
| 10,307,280 B2 | 6/2019 | Zeiner et al. | |
| 10,420,665 B2 | 9/2019 | Sharma et al. | |
| 10,548,753 B2 | 2/2020 | Rousseau | |
| 10,952,733 B2 | 3/2021 | Baron et al. | |
| 12,082,815 B2 * | 9/2024 | Baron | A61B 17/3478 |
| 2002/0123698 A1 | 9/2002 | Garibotto et al. | |
| 2006/0016195 A1 | 1/2006 | Dalla Betta et al. | |
| 2006/0237022 A1 | 10/2006 | Chen et al. | |
| 2008/0208224 A1 | 8/2008 | Surti et al. | |
| 2010/0069933 A1 | 3/2010 | D'Arcangelo et al. | |
| 2010/0292729 A1 | 11/2010 | Aguirre et al. | |
| 2011/0130775 A1 | 6/2011 | Tacchino et al. | |
| 2012/0296257 A1 | 11/2012 | Van Dam et al. | |
| 2014/0236064 A1 * | 8/2014 | Binmoeller | A61F 5/0076 604/8 |
| 2016/0100971 A1 * | 4/2016 | McGuckin, Jr. | A61F 2/04 604/8 |

FOREIGN PATENT DOCUMENTS

| | | |
|---|---|---|
| JP | 2008049157 A | 3/2008 |
| JP | 4477382 B2 | 6/2010 |
| JP | 5449534 B2 | 3/2014 |
| JP | 2016507333 A | 3/2016 |
| JP | 2017521223 A | 8/2017 |
| WO | 2006048906 A1 | 5/2006 |
| WO | 2012150578 A1 | 11/2012 |
| WO | 2016014644 A1 | 1/2016 |

OTHER PUBLICATIONS

International Search Report and Written Opinion for International Application No. PCT/US2019/013064, dated Apr. 17, 2019. (14 Pages).

* cited by examiner

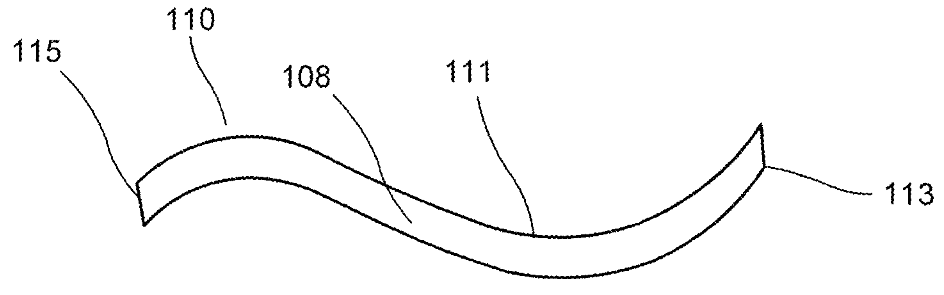
F I G. 1
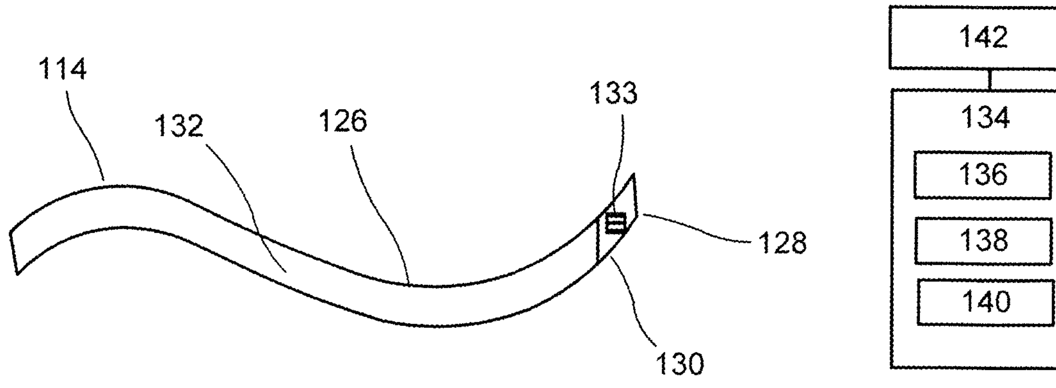
F I G. 2
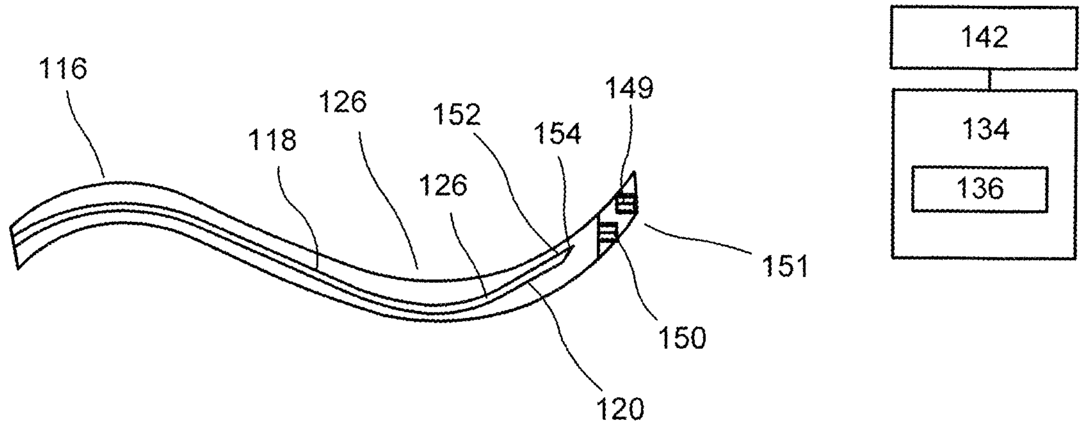
F I G. 3

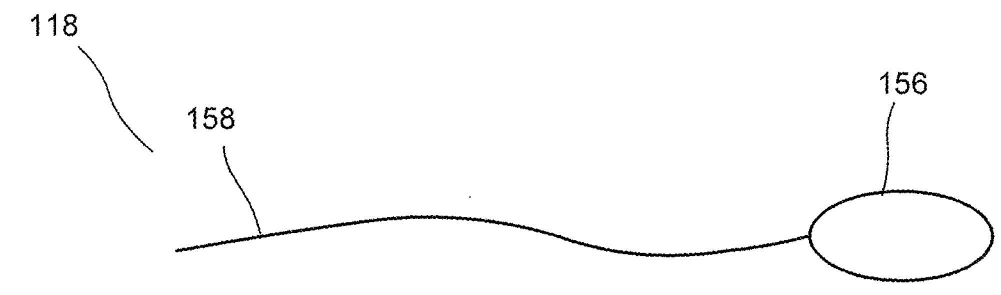
F I G. 4
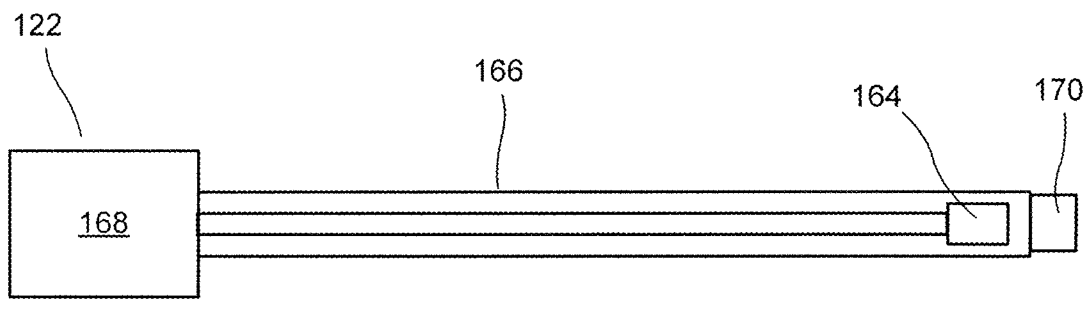
F I G. 5
164
172
178
174
176
F I G. 6

103
116
132
102
105
114
104

116
103
102
114
128
120
104
132
156
105
158
118

116
103
102
120
114
104
156
105
160
162
118

SYSTEMS, METHODS AND DEVICES FOR CONNECTING NON-ADHERENT STRUCTURES

PRIORITY CLAIM

This application is a continuation of and claims the benefit of the earlier filing date of U.S. patent application Ser. No. 17/164,329, filed Feb. 1, 2021, which claims the benefit of the earlier filing date of U.S. patent application Ser. No. 16/244,859, filed Jan. 10, 2019, which claims the benefit of priority under 35 U.S.C. § 119 to U.S. Provisional Application Ser. No. 62/616,217, filed Jan. 11, 2018, which applications are incorporated herein by reference in their entireties for all purposes. Any and all priority claims identified in the Application Data Sheet, or any correction thereto, are hereby incorporated by reference under 37 C.F.R. § 1.57.

FIELD OF THE INVENTION

The present invention relates to systems, methods and devices for suturing organs of human body and more specifically with systems, methods and devices for performing gastroenteral anastomoses.

BACKGROUND

Gastroenteral anastomoses have been performed to treat malnutrition associated with gastric outlet obstruction as well as other issues. A gastroenteral anastomosis may be created surgically, either laparoscopically or through an open surgical procedure. However, performing this procedure endoscopically entails many challenges including the need to endoscopically locate a desired position in the small bowel via the gastric lumen. Although ultrasound endoscopes have been used to provide images through the gastric and enteral walls, the small bowel is typically deflated and difficult to access in this manner.

Techniques for alleviating this targeting challenge have included using a tracking balloon passed through the pylorus deep into the duodenum or the proximal portion of the jejunum near the ligament of Trietz. The targeting balloon is then inflated with contrast medium or with water or air which provide clearer visualization by ultrasound endoscopy and/or fluoroscopy. A second method employs two similarly sized balloons axially separated from one another (i.e., along a longitudinal axis of the device) by approximately 200 mm. A space within the device extending between these balloons is then filled with dilute contrast medium creating a target for the puncture from the gastric lumen. An advantage of the two-balloon method is that the balloon itself is not punctured, as is the case with a single target balloon because the physician is puncturing between the balloons and not directly into either of them. Another method includes flooding the small bowel with diluted contrast to distend and visualize the small bowel. When the small bowel is pharmaceutically immobilized, a temporary target is created. But over time the fluid dissipates and needs to be reintroduced.

A second challenge posed by endoscopic gastroenterostomy is the potential to lose control of a distal portion of the tissue after the initial penetration has been made. This may become more serious if the initial puncture site has been dilated with either a balloon or electrocautery.

SUMMARY

The present disclosure relates to a system for forming an anastomosis between first and second sections of a digestive tract comprising an optical scope device including a lumen extending therethrough configured to be positioned at a first target site within the first section, the optical scope device including an imaging component at a distal end thereof for viewing the first target site and a first endoscope including a working channel extending therethrough configured to be positioned at a second target site within the second section in combination with a capture device extending from a proximal end to a distal end including a loop, the capture device configured to extend through the lumen of the optical scope device and a first flexible element configured to extend through the first endoscope, the first flexible element including a coupling element at a distal end thereof, the coupling element being configured to be passed through the loop to couple the first flexible element to the capture device, connecting the first and second sections, the coupling element being movable between an insertion configuration in which the coupling element is sized to pass through the loop of the capture device and an locking configuration in which the coupling element is configured to prevent the expandable element from passing through the loop, removably locking the first flexible element wire to the capture device. The system also includes a stent including a body portion, a proximal flange and a distal flange, the body portion including a lumen extending therethrough and configured to extend through walls of the first and second target sites so that the lumen provides fluid communication between the first and second sections.

In an embodiment, the system further includes a stent delivery system including a catheter extending from a distal end to a proximal end coupled to a handle, the catheter including a working channel configured to receive the stent therein, the stent delivery system configured to position the stent within the target anastomosis site.

In an embodiment, the first section is within the small intestine.

In an embodiment, the second section is within the stomach.

In an embodiment, the system further includes a needle positioned within the working channel of the first endoscope, the needle including a lumen extending therethrough and configured to be advanced through the walls of the first and second target sites until a distal end thereof, positioned within the second section of the digestive tract, is positioned within the loop, the lumen configured to receive the first guide wire.

The present disclosure also relates to a method for forming an anastomosis between a first section of the digestive tract and a second section of the digestive tract. The method includes advancing an optical scope device including a lumen extending therethrough to a first target site within the first section of the digestive tract, the optical scope device including an imaging component at a distal end thereof for viewing the first target site, advancing a first endoscope including a working channel extending therethrough to a second target site within the second section of the digestive tract, coupling a first guide wire extending through the first endoscope to a capture device extending through the optical scope device to connect the first and second sections of the digestive tract, the first guide wire being passed from the first section to the second section through walls of the first and second target sites, the imaging component providing a visual feed of the first target site to facilitate the coupling of the first guide wire and capture device, positioning the stent in a target anastomosis site so that a distal flange of the stent is positioned within the first section, a proximal flange is positioned within the second section, and a body portion bridges the walls of the first and second target sites, a lumen of the body portion allowing for fluid communication between the first and second sections.

In an embodiment, the capture device is a snare device.

In an embodiment, the method further includes inserting the snare device through the lumen of the optical scope device until a distal end thereof extends distally past the distal end thereof, the snare device including a distal loop configured to be movable between an expanded configuration and a tightened configuration.

In an embodiment, the method further includes advancing a needle from the working channel of the first endoscope through a wall of the first target site and a wall of the second target site until a distal end thereof, positioned within the second section of the digestive tract, is positioned within the loop.

In an embodiment, the method further includes inserting the first guide wire through a lumen of the needle until a distal end of the guide wire extends through the loop and tightening the loop around the first guide wire to create a connection between the first and second sections.

In an embodiment, the method further includes infusing a volume of liquid into the first target site to increase the diameter of the first section and provide an image of the target lumen via ultrasound to assist a user visualizing the first target site.

In an embodiment, the stent is positioned within the target anastomosis site via a stent delivery system, the stent delivery system including a catheter extending from a distal end to a proximal end coupled to a handle, the catheter including a working channel configured to receive the stent therein.

In an embodiment, the method further includes passing the distal end of the catheter through the walls of the first and second target sites, deploying the distal flange of the stent so that the distal flange abuts the wall of the first target site within the first section, retracting the catheter through the walls of the first and second target sites to a position within the second section and deploying the proximal flange of the stent so that the proximal flange abuts a wall of the second target site within the second section.

In an embodiment, a distal end of the guide wire includes an anchor portion, the anchor portion extending perpendicular to a longitudinal axis of the first guide wire to form a T-shape.

In an embodiment, the method further includes advancing a second endoscope including a working channel extending therethrough to the first section, passing a second guide wire through the working channel of the second endoscope until a distal end thereof is positioned at the first target site, withdrawing the second endoscope from the patient, advancing the optical scope device over the second guide wire to the first target site and withdrawing the second guide wire from the patient.

The present disclosure also relates to a method for forming an anastomosis between a first section of the digestive tract and a second section of the digestive tract. The method includes determining a first target site within a first section of the digestive tract via an imaging component of an optical scope device, the imaging component providing a user with a visual feed of the first target site, the optical scope device including a lumen extending therethrough and having a distal end positioned at the first target site, determining a second target site within a second section of the digestive tract via an ultrasound endoscope, the ultrasound endoscope including a working channel and having a distal end positioned at the second target site, forming a connection between the first and second sections of the digestive tract by passing a distal end of a guide wire from the ultrasound endoscope through the second target site to the first target site through walls of the first and second target sites until the distal end is positioned within a capture mechanism extending from the optical scope device, the capture mechanism being positioned at the first target site and deploying a stent over the guide wire so that a distal flange of the stent is positioned within the first section, a proximal flange is positioned within the second section, and a body portion bridges the walls of the first and second target sites, a lumen of the body portion allowing for fluid communication between the first and second sections.

In an embodiment, the method further includes transilluminating the first and second target sites through walls of the first and second target sites via a light source at the distal end of the optical scope device to assist a user in visualizing the desired location of the anastomosis.

In an embodiment, the method further includes providing the user with an ultrasound image, via the ultrasound endoscope, of the transillumintated first and second target sites.

BRIEF DESCRIPTION

FIG. 1 depicts a perspective view of an endoscope of a system and method according to an exemplary embodiment of the present disclosure;

FIG. 2 depicts a schematic, partially cross-sectional view of an optical scope device of a system and method of FIG. 1;

FIG. 3 depicts a schematic, partially cross-sectional view of an ultrasound endoscope of the system and method of FIG. 1;

FIG. 4 depicts a perspective view of a snare device according to an exemplary embodiment of the system and method of FIG. 1;

FIG. 5 depicts a partially cross-sectional view of a stent delivery system of the system and method of FIG. 1;

FIG. 6 depicts a perspective side view of a stent of the system and method of FIG. 1;

DETAILED DESCRIPTION

Figures 7, 8, 9:
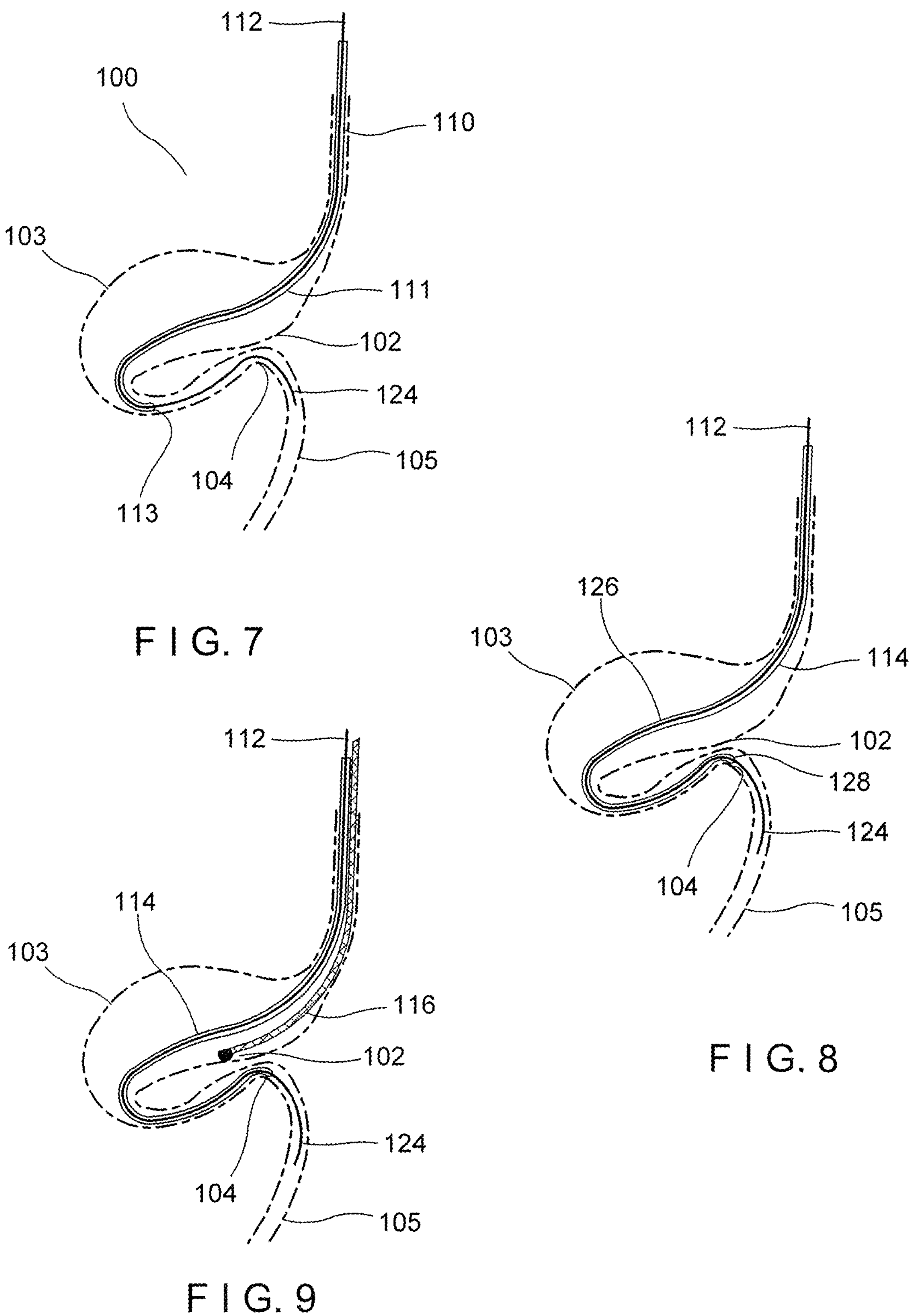
FIG. 7 depicts a partially cross-sectional view of a method step for forming an anastomosis according to an exemplary embodiment of the present disclosure.
FIG. 8 depicts a partially cross-sectional view of a method step for forming an anastomosis.
FIG. 9 depicts a partially cross-sectional view of a method step for forming an anastomosis.

The present disclosure may be further understood with reference to the following description and the appended drawings, wherein like elements are referred to with the same reference numerals. The present disclosure relates to a system and method for endoscopically connecting non-adherent structures. Specifically, the present disclosure relates to a system and method for creating a gastroenteral anastomosis. Exemplary embodiments of the present disclosure describe a system including an optical scope device which provides direct visual access at the target site within the small intestine. The exemplary system also includes an ultrasound endoscope for visualizing a target site (e.g., within the stomach), as well as a guide wire system for connecting the optical scope device and the ultrasound endoscope through the walls of intervening organs (e.g., the stomach and the small intestine). It should be noted that the terms "proximal" and "distal" as used herein are intended to refer to a direction toward (proximal) and away from (distal) a user of the device.

As shown in FIG. 1, a system 100 includes an endoscope 110 including an elongate member 111 extending from a proximal end 115 to a distal end 113 and including a working channel 108 extending therethrough. The elongate member 111 is flexible, or can include a portion that is flexible, as would be understood by those skilled in the art, to allow the elongate member to be maneuvered along a tortuous path within, for example, a natural body lumen. As will be described in further detail below, the system 100 also includes an optical scope device 114, an ultrasound endoscope 116, a snare device 118, and a stent system 122.

In an exemplary embodiment shown in FIG. 2, the optical scope device 114 is a direct visualization scope such as, for example, a Spy Scope™ that allows the user to view the small intestine when the distal end of the optical scope device 114 has been inserted therein. The optical scope device 114 includes an elongate member 126 that can be inserted into a body lumen, a distal scope tip 128, and a handle that remains outside the body lumen when the scope is in use. As would be understood by those skilled in the art, the handle includes one or more control mechanisms or actuators that can be used to control and maneuver the elongate member 126 of the optical scope device 114 within the body lumen. The optical scope device 114 may also include an actuator that may be used to actuate other functions of the endoscope 20, such as to control or maneuver lenses, image detectors and/or other components associated with illuminating and/or capturing images within a body lumen. As would be understood by those skilled in the art, the distal tip 128 may be coupled to or integrally formed with a distal end portion of the elongate member 126. The distal scope tip 128 includes a housing 130 encasing imaging and/or optical components 133. For example, optical components, such as one or more lenses, an image detector, and/or a light source may be at least partially encased or embedded within the housing 130. The optical scope device 114 may also include one or more lumens 132 extending through the elongate member 126 and/or the handle. In some embodiments, the elongate member 126 of the optical scope device 114 includes a single lumen 132 through which various components may be inserted to the target area. For example, the optical scope device 114 may include one or more working channels or lumens 132 sized and shaped to slidably receive various medical devices or tools, such as, for example, the guide wire 112, irrigation and/or suction devices, forceps, drills, snares, needles, etc.

A system controller 134 may be coupled to the optical scope device 114 and configured to control various elements of the optical scope device 114 as described in more detail below. As would be understood by those skilled in the art, the system controller 134 may include, for example, a processor 136, an image controller 138, and a light controller 140. The light controller 140 may include, for example, an external light source providing light to a distal end of the optical scope device 114 to illuminate target tissue to be imaged by the optical scope device 114. The image controller 138, the processor 136 and/or the light controller 140 may be coupled to an image or video display device 142 (e.g., a computer, a monitor or other known image display device) via the system controller 134 or by a separate connection. In alternative embodiments, some or all of these devices may be provided as separate components, separate from the system controller 134.

Figures 13, 14, 15:
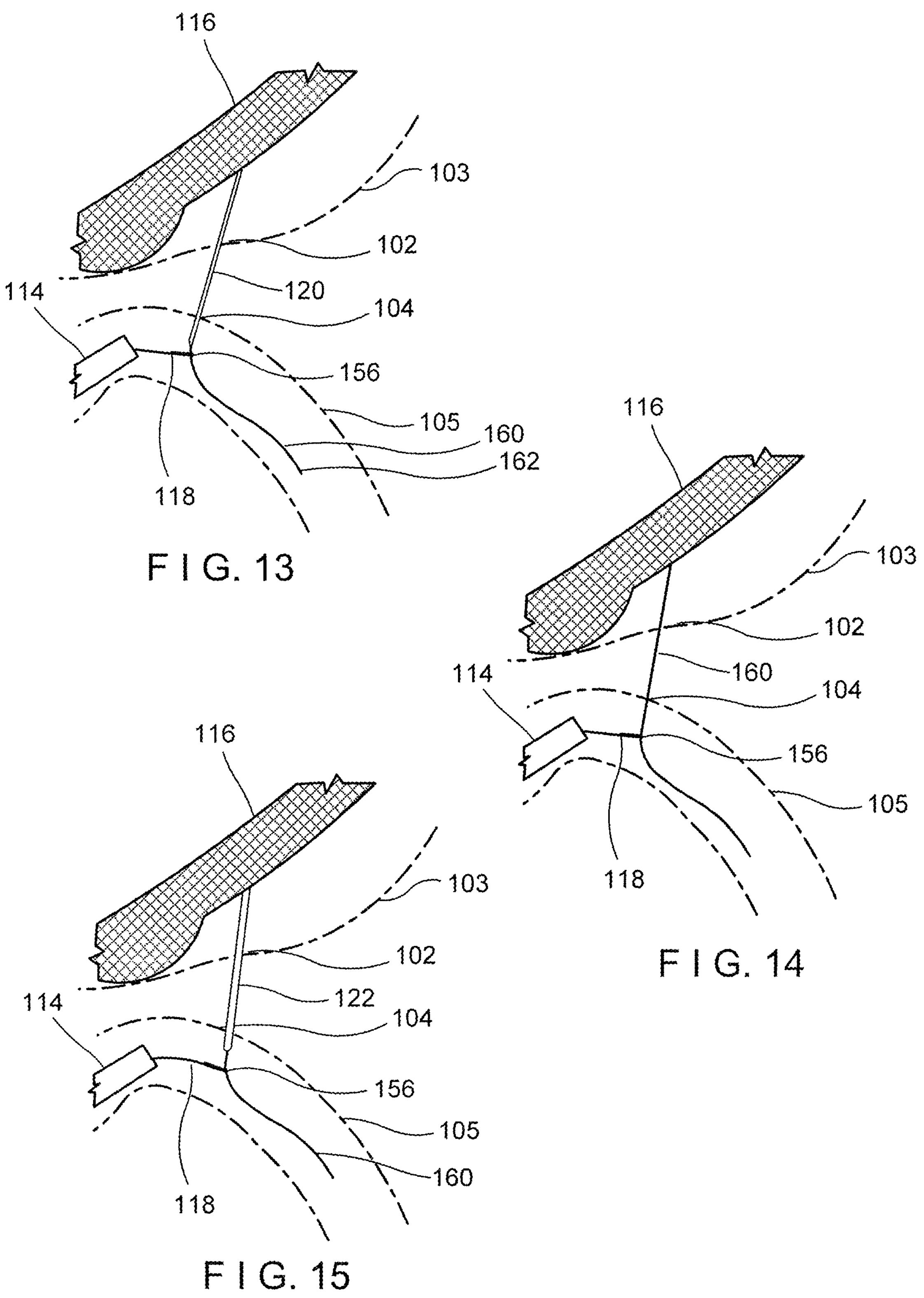
FIG. 13 depicts a partially cross-sectional view of a method step for forming an anastomosis.
FIG. 14 depicts a partially cross-sectional view of a method step for forming an anastomosis.
FIG. 15 depicts a partially cross-sectional view of a method step for forming an anastomosis.

As can be seen in FIG. 3, the ultrasound endoscope 116, in this embodiment, is a flexible endoscope extending from a proximal end to a distal end and including a working channel 148 extending therethrough. In an embodiment as would be understood by those skilled in the art, the ultrasound endoscope 116 may include forward and/or oblique viewing optics 149 adjacent to the distal end 151 of the working channel for viewing the area adjacent to the open distal end of the working channel 148. The ultrasound endoscope 116 also includes an ultrasonic transducer 150 at its distal end for providing an ultrasonic image of the stomach wall and surrounding area. A needle 120 is housed within the working channel 148 of the ultrasound endoscope 116. The needle 120, in an embodiment, is substantially cylindrical (although any other suitable shape may be employed) and extends from a proximal end to a sharp, tissue penetrating distal point 154. A lumen 153 extends through the needle 120 to a distal opening 152 at the distal point 154. The needle 120 is longitudinally movable with respect to the ultrasound endoscope 116 between a retracted or insertion position in which a distal end of the needle 120 is fully housed within the working channel 148, as shown in FIG. 13, and an extended position in which the needle 120 extends distally past the distal end of the working channel 148, as shown in FIG. 5. The ultrasound endoscope 116 may be connected to the system controller 134, processor 136 and display device 142 as would be understood by those skilled in the art.

The snare device 118, according to an exemplary embodiment depicted in FIG. 4, includes a flexible elongate member 158 and the distal loop 156. The snare device 118 is designed to ensnare a needle or guide wire in proximity to the distal loop 156 of the snare device 118 and to be controlled by a user manipulating the elongate member 158. The elongate member 158 extends from the distal loop 156 to a proximal end which remains outside the body accessible to the user of the device and includes an actuator or other means for controlling the loop 156. For example, in an embodiment, the elongate member 158 may include a handle. The snare device 118 is adapted to be passed into the lumen 132 of the optical scope device 114 to the desired position within the small intestine. The elongate member 158 preferably has a diameter smaller than that of the optical scope device lumen 132 through which it is channeled such that the loop 156 may pass with relative case through the length of the optical scope device 114, and exit the distal end thereof. The loop 156 is expandable from an insertion configuration in which lateral portions of the loop are pressed together by the inner wall of the lumen 132 of the optical scope device 114 and an open configuration, shown in FIG. 5, in which lateral portions separate from one another (e.g., under a bias imparted to the material of the loop 156) to form an open loop—e.g., substantially circular, elliptical, etc. In some embodiments, the snare device 118 may be made from a shape memory material such as a shape memory alloy, for example, nickel titanium, also known as nitinol, or a shape memory polymer, to allow the loop 156 to easily move between the insertion and open configurations. The loop 156 is also capable of being tightened by the user to capture the tip of, for example, the needle 120, as will be described in further detail below. The snare device 118 and loop 156 may be rotated within the endoscope's instrument insertion channel by manipulating the proximal end (not shown in this embodiment) of the snare device 118 to modify the position and orientation of the loop 156 relative to the target device to be captured therein.

The system further includes a stent delivery system 122 such as, for example, the AXIOS Stent System™ available from Boston Scientific Corp. The stent delivery system 122, as shown in FIG. 5, includes a catheter 166, with the stent 164 disposed therein, and a handle 168. As can be seen in FIG. 6, the stent 164 is configured as a tubular body 172 with proximal 174 and distal 176 flanges and a central lumen 178. In an exemplary embodiment, the catheter 166 may also include a cautery distal tip 170 which aids in creating a hole in the stomach and small intestine walls for insertion of the catheter 166 and, subsequently, the stent 164.

FIG. 7 depicts part of a method for forming an anastomosis between a first portion 102 of the digestive tract and a second portion 104 of the digestive tract. In the depicted embodiments, the first portion 102 is generally depicted as the stomach 103, while the second portion 104 is depicted as a portion of the small intestine 105 to perform, for example, a gastrojejunostomy to bypass the duodenum or other portion of the small intestine. It will be understood that while the present embodiments depict the first portion 102 as the stomach 103 and the second portion 104 as the small intestine 105, the anastomosis may be formed between any other suitable portions of the digestive tract. For example, an anastomosis may also be formed between the stomach and the large intestine or between a portion of the small intestine and a portion of the large intestine.

As shown in FIG. 8, the endoscope 110 is passed through the mouth of the patient, along the esophagus, through the patient's stomach 103, through the pylorus and into the small intestine 105. The guide wire 112 is then passed down the working channel 108 of the endoscope 110 until the distal end 124 of the guide wire 112 exits the endoscope 110 and extends into the duodenum distally beyond the ligament of Treitz. Once the guide wire 112 is in a target position, the endoscope 110 is removed from the patient leaving the guide wire in the small intestine with the distal end 124 at the desired position therein. As seen in FIG. 8, the elongate optical scope device 114 is then advanced over the guide wire 112 into the small intestine.

It will be understood by those skilled in the art that once the optical scope device 114 has been advanced to a distal end of the guide wire 112 beyond the ligament of Trietz, the optical scope device 114 and the guide wire 112 may be advanced to the target anastomosis site 104 by a number of methods. For example, in one embodiment, the optical scope device 114 and the guide wire 112 are advanced simultaneously as a unit through the small intestine 105 to the target anastomosis site 104. In another embodiment, the guide wire 112 is advanced ahead of the optical scope device 114 which is then followed over the guide wire 112, repeating until both arrive at the desired location within the small intestine.

With the optical scope device 114 and the guide wire 112 at the target anastomosis location, the ultrasound endoscope 116 is introduced into the patient along the optical scope device 114 through the mouth and into the stomach. The distal end 144 of the ultrasound endoscope 116, instead of being allowed to exit the stomach via the pylorus, is directed to the side of the stomach 102 adjacent to a target site for the anastomosis. Specifically, the ultrasound endoscope 116 is leaned against the lower portion of the greater curvature of the stomach 103 to look through the gastric wall toward the small intestines, as shown in FIGS. 9-10.

In order to assist with visualization of the location of the guide wire 112 and the optical scope device 114 within the small intestine 105 and thus, the desired location of the anastomosis connection 104, the user may infuse a volume of fluid into the small intestine 105 through the lumen 132 of the optical scope device 114. The fluid increases the diameter of the small intestine in the region where the tip 128 of the optical scope device 114 is located so that the user can easily visualize the anastomosis location 104. In one embodiment, a radiopaque fluid may be used, allowing the user to employ fluoroscopy to visualize the desired region 104 of the small intestine 105. The user may also use the light source 133 of the optical scope device 114 to transilluminate the small intestine 105 and the stomach 103 to allow the ultrasound endoscope 116 to see the direction of the desired connection to be made. Alternatively, the user may use a light provided on the ultrasound endoscope 116 to transilluminate the stomach 103 and the small intestine 105 to be visualized by the camera on the optical scope device 114.

Figures 10, 11, 12:
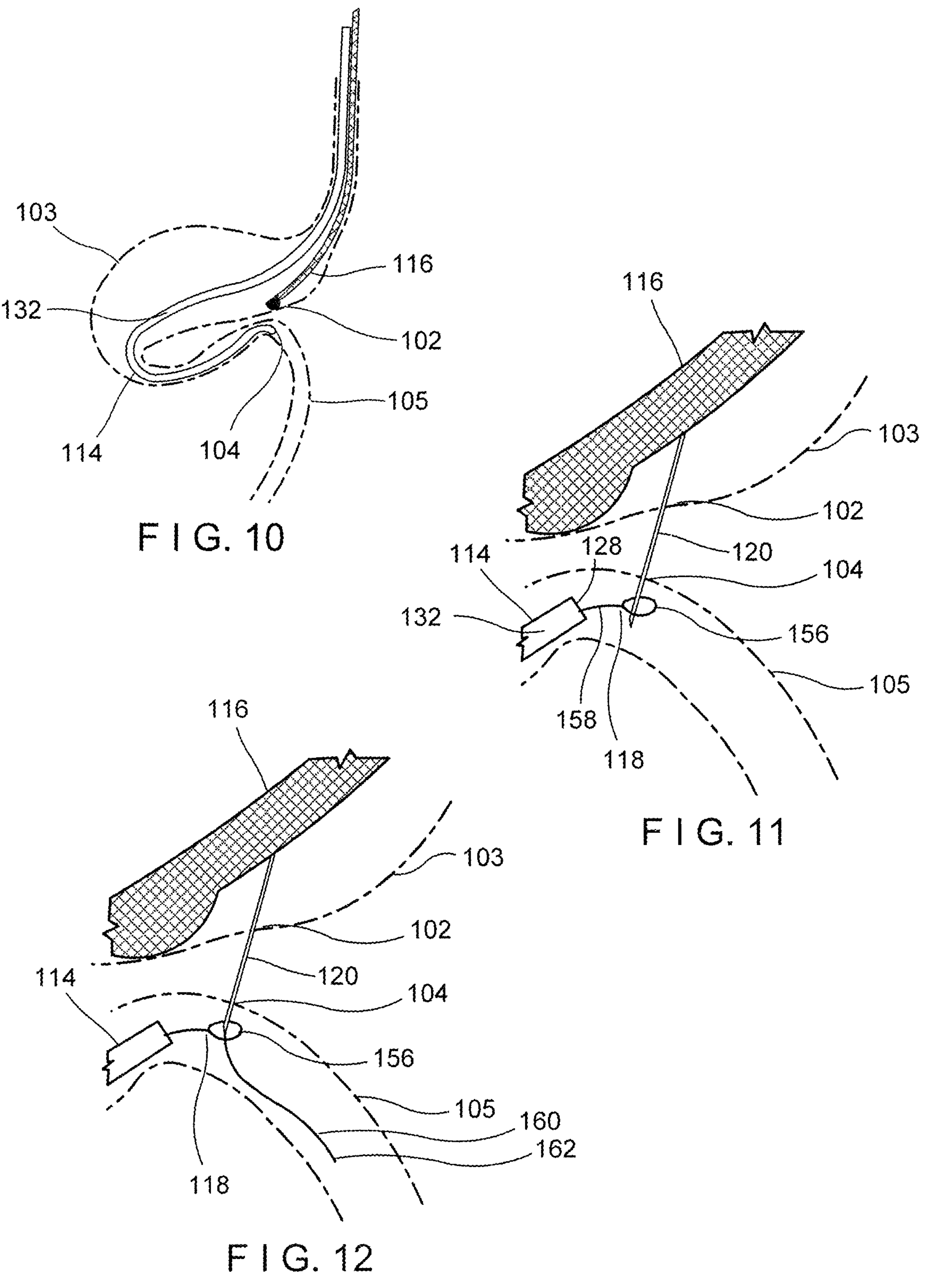
FIG. 10 depicts a partially cross-sectional view of a method step for forming an anastomosis.
FIG. 11 depicts a partially cross-sectional view of a method step for forming an anastomosis.
FIG. 12 depicts a partially cross-sectional view of a method step for forming an anastomosis.

With the ultrasound endoscope 116 in position within the stomach, the guide wire 112 may then be withdrawn from the lumen 132 of the optical scope device 114 and out of the patient, as shown in FIG. 10. The snare device 118 is then inserted through a lumen 132 of the optical scope device 114 until a loop 156 at a distal end of the snare device 118 extends distally past the distal tip 128 of the optical scope device 114 into the fluid in an open position. As those skilled in the art will understand, if there is sufficient room in the lumen 132, the guide wire 112 may alternatively be left in place as the snare device 118 is inserted therethrough.

Turning to FIG. 11, the first portion 102 and the second portion 104 can be seen in more detail. An anastomosis is to be formed between the first and second portions 102, 104. The distal end of the flexible ultrasound endoscope 116 is positioned adjacent to the stomach wall portion 102 while the distal ends of the optical scope device 114 and snare 118 are positioned adjacent to the small intestine second portion 104. When it is desired to commence formation of the anastomosis, the needle 120 is extended distally out of the working channel and pushed through the stomach wall at the first portion 102 and then through the small intestine second portion 104. The distal end of the snare device 118 is then manipulated by the user until the loop 156 is positioned around a distal portion of the needle 120. The loop 156 is then tightened around the needle 120 via proximal movement of the elongate member 158.

In order to form a stable connection between the stomach 103 and the small intestine 105, a second guide wire 160 is inserted through the lumen 150 of the needle 120 until a distal end 162 of the guide wire 160 extends distally out of the lumen 150 and into the small intestine 105, as can be seen in FIG. 11. When a desired amount of the guide wire 160 has been advanced beyond the tip of the needle 120, as visualized by the optical scope device 114, the snare loop 156 is loosed via distal movement of the elongate member 158 and repositioned on the guide wire 160, where the loop 156 is retightened to create a connecting rail between the first and second portions 102, 104, as depicted in FIG. 12-13. This stable connection provides the user with control from both ends of the anastomosis (i.e., from within the small intestine as well as within the stomach). After the guide wire 160 has been successfully captured by the snare loop 156, the needle 120 may be retracted from the small intestine and the stomach through the working channel of the ultrasound endoscope 116, leaving the guide wire 160 and snare device 118 connected through the walls of the stomach and small intestine, as shown in FIG. 14.

In an exemplary embodiment, the guide wire 160 may include a balloon or other expandable element at a distal end thereof to prevent the snare loop 156 from sliding off after capture of the guide wire 160. Specifically, the snare loop 156 is positioned over the guide wire 160, proximally of the balloon. The balloon is then inflated with either a fluid or a gas to a size larger than a size of the opening of the snare loop 156, preventing the loop 156 from disengaging from the guide wire 160.

Figure 17:
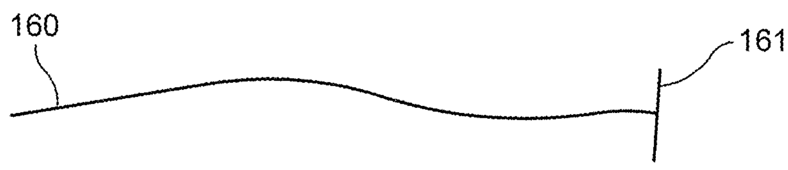
FIG. 17 depicts a perspective view of T-wire extension for a guide wire of the system and method of FIG. 1.

In another exemplary embodiment, the guide wire 160 includes a T-wire extension 161 at the distal end 162, as shown in FIG. 17. Specifically, the distal end includes an anchor portion 163 that extends perpendicular to a longitudinal axis, L, of the guide wire 160, forming a T-shape. When the guide wire 160 is positioned with the lumen 150 of the needle 120, the anchor portion 163 is constrained to an insertion configuration in which the anchor 163 is substantially parallel to the guide wire 160. However, then the distal end 162 of the guide wire 160 is advanced distally past the distal end of the needle 120, the extension 161 moves (e.g., under its natural bias) to its deployed configuration with the anchor portion 163 perpendicular to the guide wire 160. Thus, this T-wire extension 161 with the anchor 163 prevents the snare from inadvertently sliding off of the guide wire 160.

Figure 16:
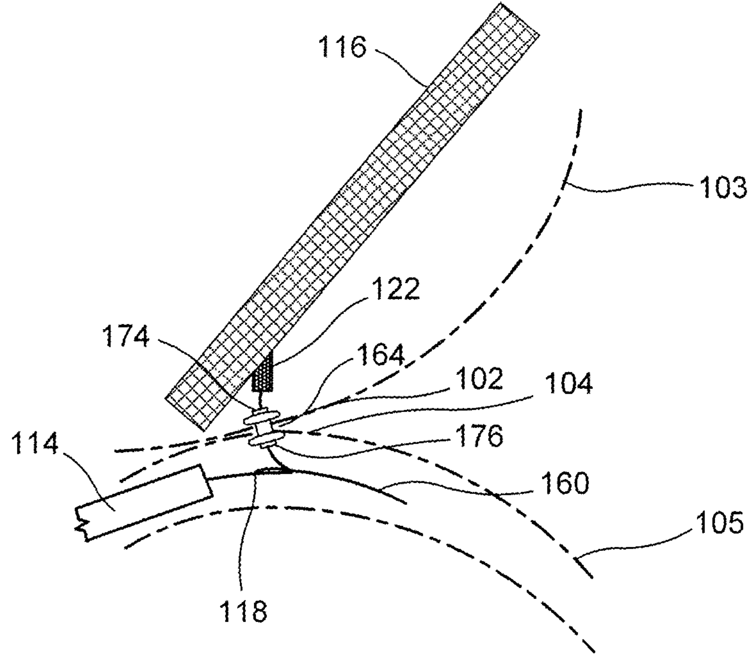
FIG. 16 depicts a partially cross-sectional view of a method step for forming an anastomosis.

With the connection in place, a stent 164 may be positioned at the anastomosis site using the stent delivery system 122. The catheter 166 is advanced over the guide wire 160 through the working channel 148 of the ultrasound endoscope until the distal tip reaches the wall of the stomach 103, as shown in FIG. 15. At this point, if the catheter 166 includes a cautery distal tip 170, the user may turn on the electrical energy supply to the tip 170 so that as the catheter 166 is advanced distally, a small hole is formed through the stomach and the small intestine walls. The catheter 166 is advanced until visible by the optical scope device 114 within the small intestine. Once the catheter 166 is in a desired position at the site of the anastomosis, the distal flange segment 176 of the stent 164 is deployed from the distal end of the catheter 166 via an actuator on the handle 168 as would be understood by those skilled in the art. Once the distal flange 176 is in place adjacent to the wall of the small intestine 105 at the target portion 104, the catheter 166 is retracted, drawing the stomach and intestine walls together. The proximal flange 174 of the stent 164 is then deployed within the stomach 103 at the target portion 102. Thus, at this point the entire stent 164 is deployed with the distal flange 176 within the small intestine 105, the proximal flange 174 within the stomach 103 and the tubular body 172 bridging the small intestine and stomach walls, as shown in FIG. 16. The flanges 174, 176 prevent migration of the stent 164 from the anastomosis point while maintaining tissue apposition between the stomach 103 and small intestine 105 while the lumen of the tubular body 172 allows for fluid communication between the two organs.

With the anastomosis complete, the stent system 122 may be retracted out of the body. The snare loop 156 is then loosened and the guide wire 160 and ultrasound endoscope 116 are removed from the body, followed by the optical scope device 114 and snare device 118.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather modifications are also covered within the scope of the present invention as defined by the appended claims.

What is claimed is:

1. A system for forming an anastomosis between a first target site in a first section of a digestive tract and a second target site in a second section of the digestive tract separated from the first section by at least one anatomical wall, the system comprising:

- a first flexible elongate member configured to extend into the first section of the digestive tract and having a proximal end and a distal end;
- a needle including a lumen extending therethrough and configured to extend from the second section of the digestive tract into the first section of the digestive tract through the at least one anatomical wall;
- a first flexible element configured to extend through the lumen of the needle and the at least one anatomical wall and into the first section of the digestive tract, and having a proximal end and a distal end; and
- a stent advanceable to extend through the at least one anatomical wall and between the first section and the second section of the digestive tract;

wherein the distal end of the first flexible element and the distal end of the first flexible elongate member are configured to be connected together to create a connecting rail between the first section and the second section of the digestive tract.

2. The system of claim 1, wherein the stent comprises a body portion, a proximal flange, and a distal flange, the body portion including a lumen extending therethrough configured to provide fluid communication between the first section and the second section.

3. The system of claim 1, wherein the first section is within the small intestine.

4. The system of claim 1, wherein the second section is within the stomach.

5. The system of claim 1, wherein the distal end of the first flexible elongate element includes a loop.

6. The system of claim 5, wherein the first flexible element includes a coupling element at the distal end thereof configured to be coupled with the loop of the first flexible elongate member.

7. The system of claim 6, wherein the coupling element is movable between an insertion configuration in which the coupling element is sized to pass through the loop of the first flexible elongate element, and a locking configuration preventing the coupling element from passing out of the loop, thereby removably locking the first flexible element and the first flexible elongate element together.

8. The system of claim 5, wherein the needle is configured to be advanced through the at least one anatomical wall until a distal end of the needle, positioned within the first section of the digestive tract, is positioned within the loop.

9. The system of claim 8, wherein the first flexible element is extendable through the lumen of the needle and through the loop to create a connecting rail between the first section and the second section.

10. The system of claim 9, wherein the first flexible element includes a coupling element at the distal end thereof configured to be passed through the loop to couple the first flexible element to the first flexible elongate member.

11. The system of claim 10, wherein the coupling element is movable between an insertion configuration in which the coupling element is sized to pass through the loop of the first flexible element, and a locking configuration in which the coupling element is configured to be prevented from passing out of the loop, thereby removably locking the first flexible element and the first flexible elongate member.

12. The system of claim 5, wherein the first flexible element is a guidewire with an expandable element at the distal end movable between an insertion configuration in which the expandable element is sized to pass through the loop of the first flexible element, and a locking configuration in which the coupling element is configured to be prevented from passing out of the loop, thereby removably locking the first flexible element and the first flexible elongate member.

13. The system of claim 1, wherein the first flexible element has a coupling element at a distal end thereof configured to be coupled with the first flexible elongate member.

14. A system for forming an anastomosis between a target site in a first section of a digestive tract and a target site in a second section of a digestive tract separated from the first section by at least one anatomical wall, the system comprising:

- a first flexible elongate member configured to extend into the first section of the digestive tract and having a proximal end and a distal end;
- a needle including a lumen extending therethrough and configured to extend from the second section of the digestive tract into the first section of the digestive tract through the at least one anatomical wall;
- a first flexible element configured to extend through the lumen of the needle and the at least one anatomical wall and into the first section of the digestive tract, and having a distal end and a proximal end; and
- a stent delivery system configured to deliver a stent to the digestive tract and to extend the stent through the at least one anatomical wall to extend between the first section and the second section of the digestive tract;
- wherein the distal end of the first flexible element and the distal end of the first flexible elongate member are configured to be connected together to create a connecting rail between the first section and the second section of the digestive tract.

15. The system of claim 14, further comprising a stent configured to extend through walls of the first section and the second section of the digestive tract.

16. The system of claim 15, wherein the stent comprises a body portion, a proximal flange, and a distal flange, the body portion including a lumen extending therethrough configured to provide fluid communication between the first section and the second section.

17. The system of claim 14, wherein the stent delivery system comprises a catheter extending from a proximal end coupled to a handle to a distal end positionable within the second section, the catheter including a working channel configured to receive a stent therein, the stent delivery system configured to position the stent through the at least one anatomical wall.

18. A system for forming an anastomosis between a target site in a first section of a digestive tract and a target site in a second section of the digestive tract separated by at least one anatomical wall, the system comprising:

- a snare configured to extend into the first section of the digestive tract and having a distal end with a loop and a proximal end;
- a needle having a proximal end and a distal end and defining a lumen extending therebetween, the needle configured to extend into the second section of the digestive tract through the at least one anatomical wall; and
- a stent advanceable, using the system, to extend through the at least one wall of the first section and the second section of the digestive tract;
- wherein the loop of the snare is configured to be positioned around the distal end of the needle to create a connecting rail between the first section and the second section of the digestive tract.

19. The system of claim 18, wherein the loop of the snare is configured to be positioned around the distal end of the needle within the first section of the digestive tract.

20. The system of claim 18, further comprising a first flexible element extendable through the lumen of the needle and into the first section of the digestive tract, wherein the loop of the snare is configured to be positioned around a distal end of the first flexible element to create a connecting rail between the first section and the second section of the digestive tract.

* * * * *